United States Patent [19]
Andreiko et al.

[11] Patent Number: 5,474,448
[45] Date of Patent: Dec. 12, 1995

[54] LOW PROFILE ORTHODONTIC APPLIANCE

[75] Inventors: Craig A. Andreiko, Alta Loma; Mark A. Payne, Whittier, both of Calif.

[73] Assignee: Ormco Corporation, Glendora, Calif.

[21] Appl. No.: 285,941

[22] Filed: Aug. 4, 1994

Related U.S. Application Data

[63] Continuation-in-part of Ser. No. 973,973, Nov. 9, 1992, which is a continuation-in-part of Ser. No. 775,589, Oct. 15, 1991, abandoned, and a continuation-in-part of Ser. No. 875,663, Apr. 29, 1992, abandoned, which is a continuation of Ser. No. 467,162, Jan. 19, 1990, Pat. No. 5,139,419.

[51] Int. Cl.$^6$ .................................................. A61C 3/00
[52] U.S. Cl. ................................................. 433/24; 433/8
[58] Field of Search ............................ 433/24, 8, 9, 16, 433/17, 20

[56] References Cited

U.S. PATENT DOCUMENTS

| | | | |
|---|---|---|---|
| 3,477,128 | 11/1969 | Andrews | 433/16 |
| 3,660,900 | 5/1972 | Andrews | 433/16 |
| 3,881,252 | 5/1975 | Andrews | 433/16 |
| 4,249,897 | 2/1981 | Anderson | 433/16 |
| 5,011,405 | 4/1991 | Lemchem | 433/24 |
| 5,139,419 | 8/1992 | Andreiko et al. | 433/24 |

OTHER PUBLICATIONS

Catalog: Ormco Orthodontic Products, pub. by Ormco Corporation, 1990 Sec. 1, 2 & 3.
Catalog: 3M Unitek Orthodontic Product, pub. by 3M 1–1 to 1–55.
Catalog: Rocky Mountain Orthodontics Cat. #4, pub. by RMO, Inc. E–1 to E–62.
Catalog: Orthodontics pub. by Dentaurum, Inc. pp. 1–58.

*Primary Examiner*—Cary E. O'Connor
*Attorney, Agent, or Firm*—Wood, Herron & Evans

[57] ABSTRACT

A low profile orthodontic appliance and method of designing custom and standard low profile orthodontic appliances are provided. The archwire of the appliance is not parallel to the dental archform but converges toward the archform preferably in the vicinity of the incisors. Slotted brackets on either the laterals, the cuspids or the first bicuspids have mesially rotated slots to support the archwire in sloped relation to the teeth. For standardized appliances, the slot rotation may be provided only in brackets for the upper laterals and the lower cuspids. For Caucasians, the preferred rotation angles are 4.5 and 6 degrees respectively. For Asians, the rotation angles are preferably distributed over brackets for the laterals, cuspids and first bicuspids. Tooth to archwire spacing is not more than 0.05 inches for all teeth but the upper laterals. The archwire shape is designed in custom appliances by digitizing tooth shape of a patient, calculating ideal finish tooth positions and ideal bracket positioning, designing an optimally smooth archwire spaced optimally close to the teeth and manufacturing brackets with calculated slot rotations in most of the brackets. For standardized appliances, statistically average anatomy or appliance designs follow the custom appliance design method, except that only the most significant slot rotation angles are fabricated.

16 Claims, 3 Drawing Sheets

LOW PROFILE ORTHODONTIC APPLIANCE

This application is a continuation-in-part of pending U.S. patent application Ser. No. 07/973,973, filed Nov. 9, 1992, entitled Method and Apparatus for Designing and Forming a Custom Orthodontic Appliance and for the Straightening of Teeth Therewith, which is a continuation-in-part of abandoned U.S. application Ser. No. 07/775,589, filed Oct. 15, 1991, entitled Method of Forming Orthodontic Brace, and is also a continuation-in-part of U.S. patent application Ser. No. 07/875,663, filed 29 Apr. 1992, now abandoned, entitled Method of Forming Orthodontic Brace, which is a continuation of U.S. patent application Ser. No. 07/467,162, filed Jan. 19, 1990, now U.S. Pat. No. 5,139,419, all of which are commonly owned by the assignee of the present application and all are hereby expressly incorporated into this application by reference.

FIELD OF THE INVENTION

The present invention relates to orthodontic appliances for straightening teeth. More particularly, the present invention relates to arcuate orthodontic appliance designs for presenting the lowest profile or providing optimum proximity of the appliance, particularly the archwire of an appliance, relative to the faces of the individual teeth of the patient, and for maintaining an optimal smooth arcuate shape.

BACKGROUND OF THE INVENTION

One of the paramount goals of orthodontic treatment has been to have the mesial and distal contacts of the teeth of the patient in an arch that is parallel to the dental archform. In order to achieve this with a smoothly bent archwire, orthodontic appliances have been constructed using an archwire that is shaped to an archform that is mathematically similar, or parallel, to the dental archform of the patient. However, because the different teeth of the patient are of differing thicknesses, this goal has required the use of larger brackets on the smaller teeth of the patient and, conversely, smaller brackets on the thicker teeth of the patient, so as to provide a constant spacing between the archwire and dental archform.

Providing higher profile brackets on the smaller teeth is particularly troublesome on the lower anterior teeth, which are the smallest teeth of the patient. As a result of the use of the thickest brackets on these lower anterior teeth, the appliance presents a higher profile, that is, extends farther from the tooth in the labial-lingual direction. In such higher profile appliances, the archwire is supported in a position spaced away from the face of the tooth, compromising the performance of the appliance in many ways.

For example, increased spacing of the archwire from the tooth unfavorably increases the moments about the center of resistance of the tooth. In addition, the higher profile brackets often result in the need to compromise the placement of the brackets on rotated or otherwise misaligned teeth. Furthermore, the higher profile brackets place greater loads on the bracket-to-tooth adhesive, contributing to an increase in the likelihood of failure of the bond.

Additionally, the larger brackets interfere with oral hygiene, increasing enamel decalcification and compromising gingival health.

Therefore, it is desirable to provide orthodontic appliances with brackets that provide as low a profile as possible. In the prior art, however, the need to provide a minimum archwire spacing from the thicker teeth has prevented the use of lower profile brackets on the thinner teeth, while preserving other previously accepted requirements of orthodontic appliance design.

In providing appliances having archwires that are parallel to the dental archform, the brackets employed have had slots to receive the archwires, with slot bottoms that are parallel the archform. Such slot bottoms have been generally parallel to the bracket bases so that, when the brackets are mounted on the teeth of the patient, they support the archwire and maintain the archwire and the dental archform of the teeth in a parallel relationship. One exception to the traditional bracket configuration has been in what is known as the Roth line of treatment which calls for overcorrection of the teeth by imparting a rotation of the teeth relative to the archwire. This has entailed configuring certain of the brackets so that the slots are rotated, relative to the bracket bases and the mounting surfaces of the teeth, in a positive direction, that is in a direction that spaces the mesial end of the slot farther from the tooth than the distal end. This rotation nonetheless maintains the slot bottoms and archwire parallel to the archform of the teeth. This technique of positively sloping the bracket slots for overcorrection has been employed in brackets for the cuspids and the teeth distal thereto.

The orthodontic practices of the prior art have, nonetheless, produced appliances which, when installed on the teeth of patients, have profiles that are not optimally low, and, if modified by the replacement of smaller brackets to produce a lower profile, do not function effectively to position the teeth on a suitable archform. Unwanted tooth rotation during treatment, such as to the lower cuspid result in the prior art configurations, requiring first order bends in the archwire, for example, mesial to the cuspid bracket to prevent the cuspid rotation. For these and other reasons, it is apparent that there is a need for an orthodontic appliance having a low profile and simultaneously achieving the other orthodontic appliance design objectives.

SUMMARY OF THE INVENTION

Accordingly, it is a primary objective of the present invention to provide an orthodontic appliance that is of the lowest optimal profile with respect to each of the individual teeth of the patient.

It is a particular objective of the present invention to provide such a low profile appliance having minimum profile brackets on each of the teeth to support a smoothly curved archwire.

It is still a further objective of the present invention to provide a low profile orthodontic appliance properties that can be realized in custom as well as standardized orthodontic appliances.

Additional objectives of the present invention are to provide methods of designing optimally low profile appliances and of treating patients with optimally low profile appliances.

In accordance with the principles of the present invention there is provided an orthodontic appliance having an archform that is not necessarily mathematically similar or parallel to the dental archform, but which nonetheless functions to maintain the teeth in a desired relationship to the dental archform, such as by maintaining the mesial and distal contacts or other features of the teeth in an archform characteristic of the ideal finish positions of the teeth.

In the preferred embodiment of the present invention, an arcuate appliance is provided formed of an archwire that is not parallel to the dental archform at every point, but rather converges toward the dental archform near certain teeth. Preferably, such an archwire converges toward the dental archform in the vicinity of the incisors, particularly the lower incisors. Such an archwire is preferably designed in mathematically definable by segments having curvatures and foci that differ from those of corresponding segments that will define a dental archform for the patient.

Further in accordance with the preferred embodiment of the present invention, the appliance is provided with brackets having optimally low profiles, notwithstanding that the brackets are to be mounted on smaller ones of the teeth. As a result, low profile brackets are provided for the anterior teeth, particularly the lower anterior teeth, thereby supporting the archwire portion of the appliance so that it converges with the corresponding dental archform of the patient at the front of the patients mouth.

In the preferred embodiment of the invention, the convergence of the archwire and the dental archform of the patient is accompanied by the provision of brackets that may be positioned and oriented on the teeth to horizontally extend perpendicular to the dental archform of the patient, but not necessarily to extend perpendicular to the archwire where the archwire attaches to the brackets. Accordingly, there is provided an orthodontic appliance formed of an archwire, which is shaped to converge at various points along its length with the dental archform of the patient, particularly toward the front of the mouth. In combination with the archwire are provided low profile brackets, which have slot bottoms, some of which are sloped at angles, in the archwire plane, with respect to the bracket mounting surfaces that interface with the teeth. Such angles are referred to herein, as in the practice of orthodontics, as "rotation" angles of the archwire slots of the brackets. In particular, in the preferred embodiment of the invention, one or more slots, particularly in the brackets on the three teeth that are within one tooth of the cuspids, include at least one bracket having a generally mesial rotation, that is, a slot that is sloped such its front is closer to the tooth and the bracket base than the back of the slot.

For the use of the invention in a custom orthodontic appliance, it is preferred that slot rotation be employed in any or all of the brackets to maintain the optimally low profile archwire and appliance. Generally, such rotation will be predominantly in the mesial direction, so that the archwire, particularly the lower archwire, maintains a low profile adjacent the anterior teeth.

For the use of the invention in a standardized appliance, it is preferred that the net negative rotation at least three or four degrees be provided in the brackets for the laterals, cuspids and first bicuspids for each of the upper and lower arches. Generally, for the upper arch, such rotation may be provided entirely in the upper lateral brackets, and alternatively, particularly for Asian patients, in the upper cuspid brackets and preferably also in the upper first bicuspid brackets. For the lower arch, such rotation may be confined to the cuspid brackets. With such rotations, the spacing of the archwire center from the surfaces of the teeth are generally not more than 0.050 inches on all teeth but the upper lateral, where the spacing is less than 0.010 inches greater. With such spacings and rotations, the slots of the other brackets of a standardized set may be made with no slot rotation, particularly for the centrals and second bicuspids.

Further in accordance with the preferred embodiment of the present invention, particularly where the appliance is of custom appliance design, the slot bottoms in the bracket are not only formed at rotation angles, but are further curved in the archwire plane to conform to the curvature of the archwire along its length of its contact with each of the individual brackets.

According to the method of the present invention, the appliance is designed by determining the finish positions of the teeth, whether on an individual patient basis using digitized anatomical data derived from the individual patient's teeth as in the manufacture of custom orthodontic appliances, or on a based on statistical average data as in the manufacture of standardized orthodontic appliances. Then, upon consideration of shapes of the different teeth in the mouth, the appliance is designed with appropriately positioned brackets, that establish the spacing of the tooth face and the archwire within an optimum range or "window" of each other. Then, a smoothly contoured archwire shape is calculated or selected that places the archwire within the window adjacent each of the teeth. Then, a set of brackets is designed that have slot bottoms positioned to support the archwire within the window. Then, by considering the relative positions of the slot bottoms of brackets of different teeth of the patient, particularly of adjacent teeth of the patient, slot rotation angles are calculated and slots incorporating the calculated rotation angles are formed in brackets, as set forth above. Additionally, it is preferred, particularly with custom appliances, that the rotated slots be formed with a curved slot bottom conforming to the optimal curvature of the archwire at the point of contact with the bracket, preferably by cutting the slot with a computer controlled mill that is programmed to the calculated slot rotation and curvature.

In accordance with the present invention, the low profile appliance is assembled and installed on the patient to treat maloccluded teeth of the patient by placing brackets having slot bottoms that incorporate an rotation angle, and preferably are also curved, to allow a smoothly curved archwire to maintain variable spacing along its length with the dental archform of the patient, with the brackets positioned on the teeth to cooperate with the archwire to place the selected features of the teeth in an arch that is characteristic of the dental archform, and may be parallel to that archform.

The low profile appliance of the present invention, when used in accordance with the invention in the treatment of patients, prevents the unfavorable exertion by the appliance of increased moments on the teeth about the center of resistance of the tooth. The low profile brackets avoid the need to compromise the placement of the brackets on rotated or otherwise misaligned teeth. Furthermore, the low profile brackets place smaller loads on the bracket-to-tooth bond than do brackets of appliances of the prior art, decreasing the stress on adhesives, and thereby reducing the likelihood of failure of the bond. The rotation in the brackets to support the closely fitting archwire reduces adverse cuspid rotation during treatment, avoiding the need for first order bends in the archwire mesial to the cuspid bracket. Additionally, the smaller brackets promote oral hygiene.

These and other objectives and advantages of the present invention will be more readily apparent from the following detailed description of the drawings and preferred embodiments, in which:

DETAILED DESCRIPTION OF THE PREFERRED EMBODIMENTS

Figure 1:
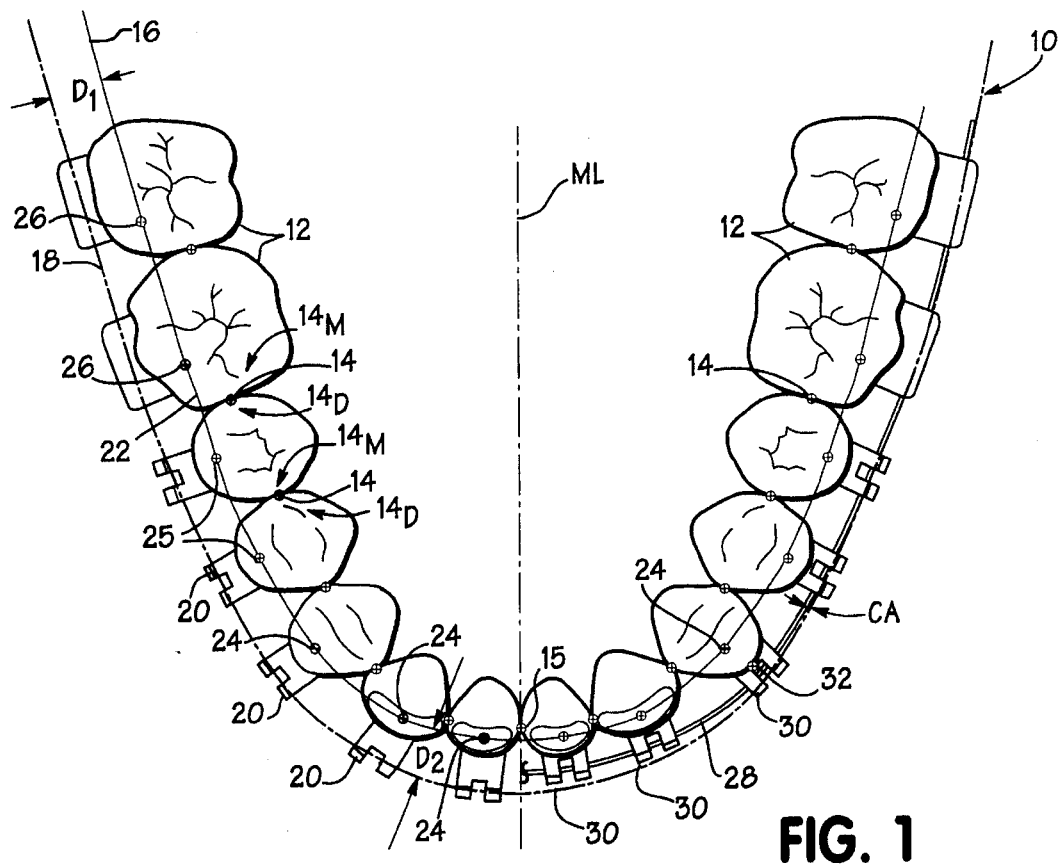
FIG. 1 is a plan view of a dental arch of a patient diagrammatically illustrating a low profile orthodontic appliance embodying principles of the present invention.

Referring to FIG. 1, a lower dental arch 10 of a patient is illustrated, in which the individual teeth 12 of the patient are arranged in ideal finish positions. In such positions, the teeth 12 are in contact with adjacent teeth at a series of contact points 14, at which a mesial contact point 14M of each tooth is in contact with a distal contact point 14D of an adjacent tooth, except for the central incisors, which have their mesial contact points in mutual contact at the center 15 of the dental arch 10. In current orthodontic practice, it has been regarded as desirable that the teeth 12, in their finish positions, form a dental arch 10 in which the teeth 12 are in contact at their respective contact points 14. Such a dental arch may be defined by as an arcuate form such as the smooth curve 16. Such an archform is generally considered to be a stable archform into which the teeth are urged into mutual contact by forces exerted by adjacent facial anatomy, or by an orthodontic appliance. The curve 16, so defined, that may be said to represent the finish dental archform, is capable of being represented by a smooth, continuous mathematical equation in two dimensional coordinates in a horizontal plane.

To achieve tooth placement that may be defined as an archform 16, the practice has been to employ an archwire that lies on an archwire curve 18 that is generally parallel to the dental archform 16, the curve 18 being offset from the archform 16 by equal distances, for example $D_1$ and $D_2$, at various points along the length of the curve 18. Such an archwire, lying on the curve 18, is supported on each of the teeth 12 by a bracket 20. The brackets 20 are mounted on the surfaces of the teeth 12 on the side facing the archwire, where the surfaces of the teeth, when in their finish positions, will be spaced at different differences from the archform 16 and the archwire curve 18 due to the differing thicknesses of the teeth. As is illustrated in exaggerated proportions in FIG. 1, in order to support an archwire of curve 18, because the teeth are of differing thicknesses, brackets 20 of differing sizes are employed for each of the teeth. Typically, the smaller anterior teeth, particularly those on the lower dental arch, require brackets that have dimensions that place the slot bottoms at greater distances form the surface of the tooth, in order to support the archwire on the curve 18 that is parallel to the assumed dental archform 16. These brackets 20 may be referred to as higher profile brackets, Referring still to FIG. 1, the dental archform 16 is preferably a more specific dental archform, which is the mandibular dental archform for the finish positions of the lower teeth that is a smooth continuous curve on which the mandibular teeth are positioned such that the incisal tips 24 of the anterior or single cusped teeth (incisors and cuspids), the buccal cusp tips 25 of the bicuspids, and the mesial buccal cusp tips 26 of the molars, are placed. For the upper teeth, a corresponding maxillary dental archform (not shown) defines the positions of marginal ridges and points on lingual surfaces of the anterior upper teeth that occlude with the points 24, 25 and 26 of the lower teeth. In addition to the mandibular dental archform 16 the upper teeth are placed on a corresponding maxillary dental archform (not shown) which represents corresponding finish tooth positions of the upper teeth (not shown). Because the archform 16 contains the points of occlusion of the lower and upper teeth, the curve 16 takes into account the stable dental archform that the forces of the occluding teeth tend to cause the teeth to assume.

Further illustrated in FIG. 1, according to the preferred embodiment of the present invention, is a low profile archwire curve 28 that defines the shape of an archwire for mounting on the teeth 12 by the use of a set of low profile brackets 30. The curve 28 for the archwire is determined so as to allow for the use of an archwire that is both smoothly curved and spaced optimally close to the surfaces of each of the individual teeth 12. Such an archwire is supported on the teeth 12 by a set of brackets 30 having optimally low profiles. The determinations of an archwire curve 28 that lies optimally close to the teeth as well as the brackets 30 and bracket geometries needed to support such an archwire are preferably achieved by the use of the method of applicants' U.S. patent application Ser. No. 07/973,973, filed Nov. 9, 1993, entitled Method and Apparatus for Designing and Forming a Custom Orthodontic Appliance and for the Straightening of Teeth Therewith, incorporated by reference above. Such application describes in detail a method by which custom orthodontic appliances are designed based on individual patient anatomy. However, for purposes of the present invention, the concepts described in that application for determining optimal archwire shape are applicable to the design of standardized orthodontic appliances based on average patient dental anatomy. The method for determining the shape of an archwire curve 28 for the design of an optimally low profile orthodontic appliance is set forth in the flowchart of FIG. 2.

Figure 2:
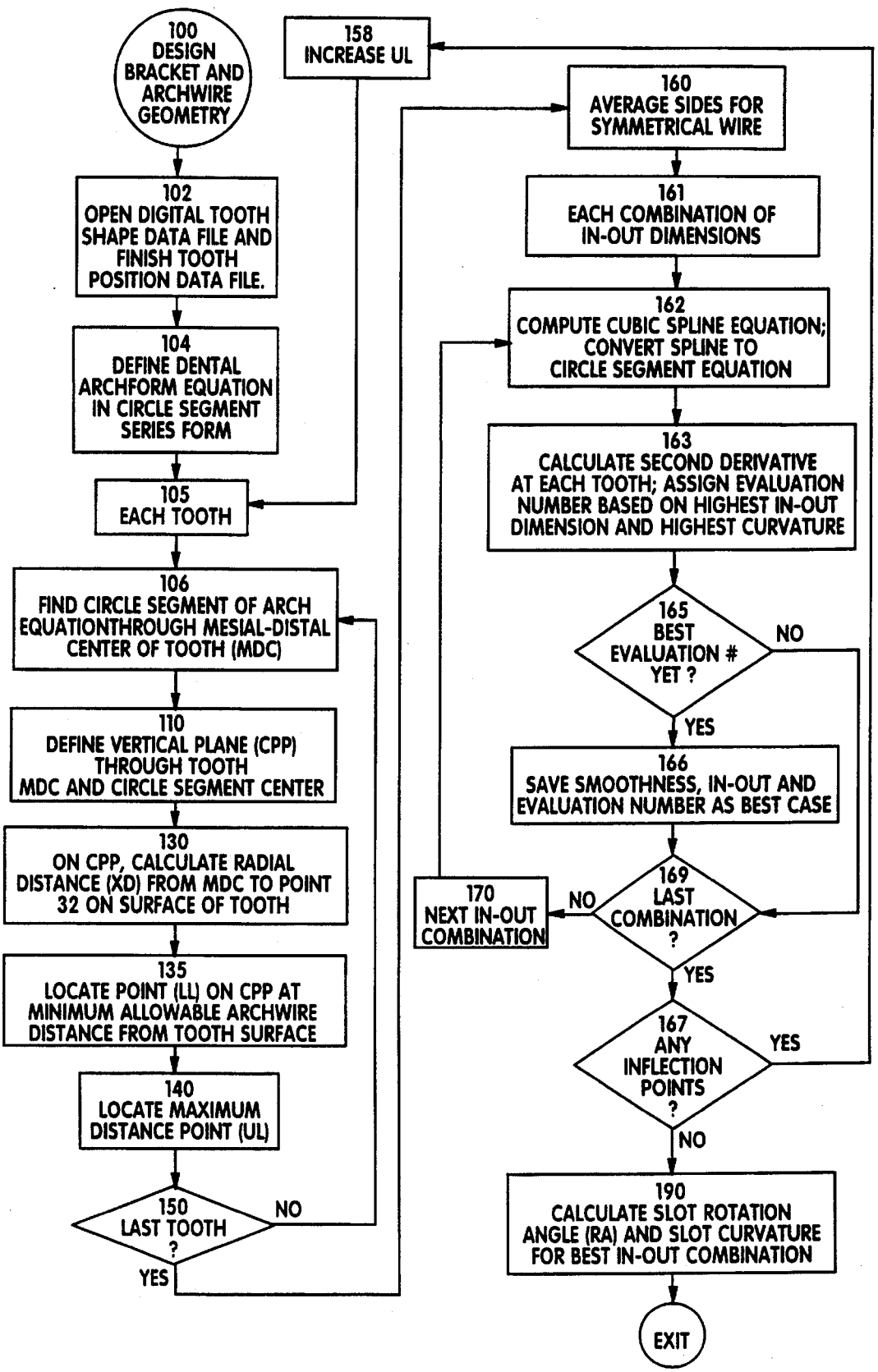
FIG. 2 is a flowchart of the steps of a computerized method for the design of the low profile appliance of FIG. 1.

In the flowchart of FIG. 2 there is illustrated a procedure (100) that can be performed in a general purpose digital computer programmed for establishing wire and bracket geometry for a low profile appliance. With such procedure (100), a mathematical equation defining the shape of the curve 28 for a low profile appliance archwire is derived, and the optimal spacing or tooth-to-archwire distances DTW (FIG. 5) are calculated that define the spacings of the archwire curve 28 from the surface of each tooth 12 on which the bracket 30 is to be mounted. Then a slot bottom rotation angle RA is calculated for each bracket. In addition, particularly for custom appliances where additional precision can be utilized, the archwire slot is formed with a bottom curvature, as represented by a radius $R_4$ in FIG. 6. Such a curvature is calculated to conform the bracket slot to the curvature of the archwire at the points of contact between the archwire and the bracket.

Referring particularly to FIG. 2, the archwire shape design method of the present invention involves the operation of a digital computer programmed to execute the procedure (100) to determine a curve 28 for an archwire, for example the mandibular archwire illustrated in FIG. 1, by calculation of a tooth-to-wire dimension DTW for each bracket slot. This calculation involves, first, the step (102) of establishing digital data in the computer defining certain dimensions or shapes of the individual teeth of the patient and defining an equation for a dental archform, such as curve 16. The establishing of digital tooth shape data may be achieved by the techniques described in U.S. Pat. No. 5,139,419, expressly incorporated herein by reference, or by one of the other the method described in applicants' U.S. patent application Ser. No. 07/973,973, referred to above and incorporated by reference herein. The tooth shape data, so established, will contain digital information from which can be calculated the horizontal distance XD between a dental archform and a point 32 on the surface of the tooth at which a bracket 30 will be mounted. This distance is illustrated, for example, on the lower right cuspid in FIG. 1, as the distance between the point XD and, for example the curve 16, which is defined in relation to some prominence or other feature of the tooth, such as through the cusp tip 24 of the cuspid.

Figure 3:
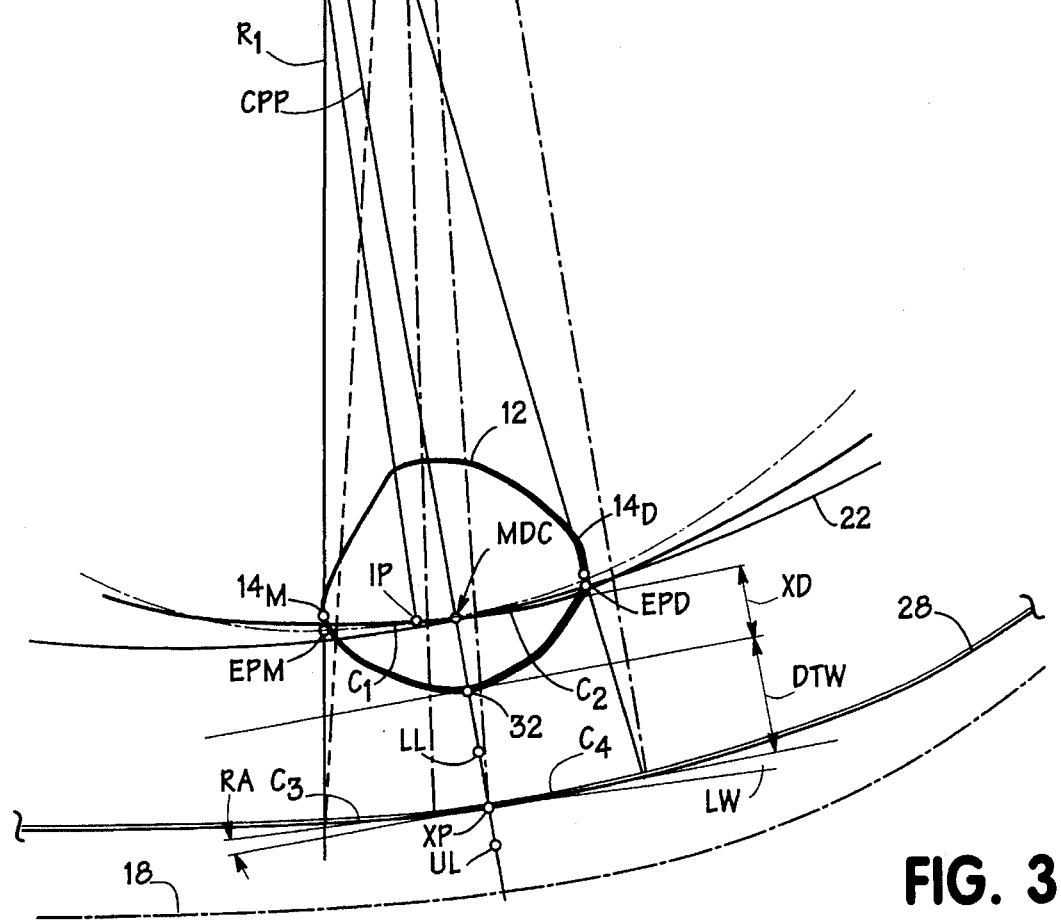
FIG. 3 is a geometric diagram illustrating parameters employed in the design method of FIG. 2.

In the next step (104), an equation is developed for the dental archform 16, preferably in the form of a statistical best fit equation, preferably defined as a series of circle segments $C_i$, each defining a segment of the dental archform curve 16. A portion of such equation for the curve 16 is illustrated in FIG. 3 where two segments $C_1$ and $C_2$ define a portion of the curve 16 that spans the arch between the contact points $14_M$ and $14_D$ of a tooth 12. In FIG. 3, where two segments $C_1$ and $C_2$ respectively define the curve 16 between one of the contact points $14_D$, $14_M$ of the tooth 12, an intermediate point IP represents the point on the archform curve 16 at which the two circle segments $C_1$ and $C_2$ intersect. Each segment $C_1$ and $C_2$, is defined respectively by a radius of curvature $R_1$ or $R_2$ from a respective circle center point CCP, $CCP_2$ and the respective arch length of the segment. The adjacent circle segments are tangent to each other at the point IP, and are tangent to the adjacent segments spanning adjacent teeth at the mesial and distal end points EPM and EPD where the radii $R_1$, $R_2$ which intersect points $14_M$, $14_D$ intersect curve 16.

The next steps (105) are performed for each tooth, beginning with the central incisor and proceeding toward the most distal tooth on the side. In step (106), the circle segment of the curve 16 on which lies the mesial-distal center or midpoint of the tooth on which the bracket is to be mounted MDC is identified. For the cuspid, this is segment $C_2$, as illustrated in FIG. 3. Then, in step (110), a center point plane CPP is created normal to the archwire plane and through the center CCP, in this case $CCP_2$, of the circle segment $C_2$ and the mesial-distal center MDC. This CPP is a line in the plan view of FIG. 3. Where the dental archform 16 is represented by the BFBCE curve as defined above, and where the tooth is, for example, an anterior tooth, the point MDC is the incisal tip 24 of the tooth which lies on the archform equation representing curve 16.

From the tooth shape data, in the next step (130), the labial distance XD is determined between the point MDC and the point 32, which is the intersection point of the line CPP with the surface of the tooth on which the bracket is to be mounted.

Still further along the line CPP from the circle segment center point CCP, two points LL and UL are defined. In step (135), the point LL is defined as a lower limit point that represents the minimum distance to be allowable between the tooth surface at point and the archwire centerline which will lie on the curve 28. In step (140), the point UL is defined as the upper limit point that represents the maximum distance to be allowable in order that the bracket satisfy the requirements of an optimally low profile appliance. Then, in step (150) the locations of these limit points LL and UL are calculated for each tooth, with (160) the coordinates of the locations of corresponding points on opposite sides of the arch being calculated and averaged to force archwire symmetry.

Preferably, the limits LL and UL are picked to establish the low profile of the appliance. For example, LL may be set at 0.036 inches and UL set at 0.052 inches. The 0.052 inches defines the maximum extension of the bracket slot in-out dimension DTW permitted, provided a sufficiently smooth curve can be constructed meeting the criteria. The 0.036 sets the minimum slot in-out dimension DTW needed for the wire to clear the teeth and for the bracket to provide adequate structural integrity. Since the dimensions of typical archwires of 0.017, 0.018 and 0.022 inch thickness, measured vertically are typically 0.025 inches thick measured horizontally, a DTW of 0.036 inches leaves about 0.026 inches from tooth to slot bottom, measured in the archwire plane. In that most brackets have mounting pads of about 0.013 inches thick for securing the bracket to the tooth, this leaves another 0.013 for structural support between the slot and the bracket base. Elimination of the pad will enable further reduction of DTW to 0.026 inches, which will leave 0.013 inches clearance between the wire and the tooth surface. The elimination of the pad in this way, where the structural requirements of the bracket can be met, is preferred.

Next, in step (161), the derivation of an equation for the smoothest curve 28 that will pass through points XP between the LL and UL points of all pairs, is begun, Preferably, as in step (166), the smoothest curve 28 is derived in the form of a cubic spline equation passing between these points on each of the teeth. To achieve the smoothest curve, the existence of any inflection points is determined and the equation is optimized until the number of inflection points is minimized. Preferably, no inflection points are permitted. The test for such points is made in step (167). To eliminate inflection points, it may be necessary to increase the upper limit UL. Determination of the smoothest curve is preferably made by (163) calculating the second derivative of the archwire archform equation at each of the bracket connection points with the archwire, and selecting the curve with smallest maximum second derivative at such points. The test may also be made by selecting the curve with the largest minimum radius of curvature at each of these connection points.

In accordance with one preferred method of determining the smoothest curve, the range from LL to UL is divided into increments, for example, 0.036, 0.040, 0.044, 0.048, and 0.052 inches. The lowest value, 0.036 is assigned to each bracket DTW, and the smoothness of the curve passing through each point at each bracket is determined. Then, (165) every combination of values of each of the brackets from central to first molar, is evaluated to determine the combination that can be satisfied by a wire of the smallest maximum second derivative. When determined, the smoothest archwire with the lowest profile is selected. This criteria may be modified to consider the curve to be the smoothest with the least variation in radius changes along the curve. In addition, instead of using the criteria of lowest profile to merely determine preferences between equally smooth curves, provided that the DTW values are between the limits LL and UL, weighting factors may be assigned to the low profile and smoothness criteria.

When the smoothest wire is selected, it is tested to insure it has no inflection points. As in step (167), if there are one or more inflection points, the process transfers to step (158), at which the points UL may be changed for one or more of the teeth based upon where the inflection occurred.

Then, the final equation for archwire shape is converted to NC machine code for producing the archwire and for cutting the brackets for the low profile appliance. For each tooth, (190) additional steps are performed. The in-out dimension DTW is determined as the distance along CPP from point 32 to the intersection point XP with curve 28 is calculated for each individual tooth, and all XP points are passed into a routine that converts the cubic spline equation to an equation of circle segment form, as used to define the dental archform equation for curve 16.

The archwire equation for the archwire curve 28 will be similar in form to the dental archform 16, defined as a series of circle segments corresponding to those of the equation for the archform 16, but with expanded and varying radii. The radii of the equation for the curve 28 will not be proportionately expanded along the curve length. Thus, the curves 16 and 28 are not everywhere parallel, and therefore many of the circle segments of the curve 28 will have different centers than those of the curve 16, as illustrated by the phantom lines in FIG. 3. The curve 28 will, in practice, normally converge toward the dental archform equation toward the front of the patient's mouth mesial of approximately the first bicuspids, for the lower arch at least. This convergence has been found to be, for example, as an angle CA which may equal approximately six degrees in the vicinity of the first bicuspid, in the example illustrated in FIG. 1. The curves 16 and 28 continue to converge as they approach the midline ML between the central incisors, about which line the curves 16 and 28 are preferably symmetrical.

Further in accordance with the present invention, to facilitate the convergence of the archwire curve 28 with the that of the dental archform 16 in the vicinity of the smaller teeth, while avoiding the imposition of unwanted rotational forces on the teeth and maintaining a smoothly contoured archwire, (190) the bottoms of the archwire slots in the brackets 30 are formed at an angle of rotation RA relative to the base of the bracket 30, as illustrated in FIG. 3. The angle RA for each bracket 30 can be calculated, as the angle between a line LP perpendicular to the line CPP and a line LW tangent to the archwire curve 28 at its intersection XP with the line CPP. This angle is also the angle between the line CPP and the radius of curvature RC of the archwire curve 28 at the point XP. Alteratively, the angle RA may be calculated precisely from the equation for the shape of the archwire curve 28 combined with the tooth shape data and information on the geometries of the bracket blanks in which the bracket slots are to be formed. Such angle RA is formed in the bracket as the angle between the bottom of the bracket slot with respect to the bracket base or the bracket mounting surface of the tooth, thereby accommodating the convergence angle between the archwire curve 28 and the dental archform. This provides a low profile archwire that is smoothly curved, which is facilitated by the provision of low profile brackets.

Figure 4:
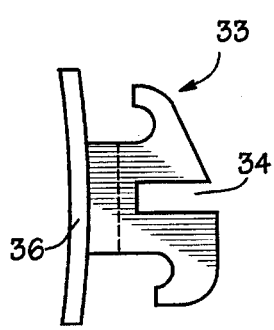
FIG. 4 is a side elevational drawing of a bracket of the low profile appliance of FIG. 1 viewing, for example, a cuspid bracket from the mesial side.
Figures 5, 6:
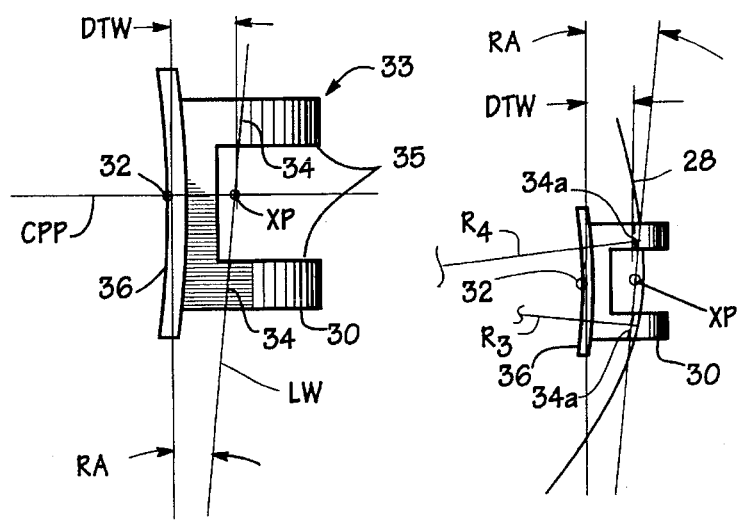
FIG. 5 is a top view of one embodiment of the bracket of the low profile appliance of FIG. 4.
FIG. 6 is a top view of an alternative embodiment of the bracket of FIG. 5.

Referring to FIGS. 4 and 5, a low profile bracket 30 for a lower cuspid is illustrated, having an archwire slot 33 therein with a slot bottom 34 spaced a distance DTW from the bracket base surface 36 which attaches to the bracket mounting surface of the tooth 12, less one half of the diameter of the archwire to be mounted in the slot 33. A slot rotation angle RA is derived by the procedure set forth in the flowchart of FIG. 2 by calculating the slope of the archwire curve 28, represented by the line LW, relative to a line perpendicular to the line CPP at its intersection point with the archwire curve 28. This slot rotation angle RA calculated for each bracket, is formed in the brackets 30 in the fabrication of the low profile appliance.

With the present invention, the low profile appliances are provided with brackets for Caucasian and Asian patients as set forth in Table 1, in which the sign of the angle RA is defined as positive where the rotation on the facial side of the tooth is in the distal direction, and is defined as negative when such rotation is in the mesial direction.

TABLE 1

|  | CAUCASIAN PATIENTS | | ASIAN PATIENTS | |
| --- | --- | --- | --- | --- |
|  | DTW (inches) | RA (°) | DTW (inches) | RA (°) |
| upper central | 0.044 | 0 | 0.050 | 0 |
| upper lateral | 0.057 | −4.5 | 0.054 | −3 |
| upper cuspid | 0.037 | 0 | 0.037 | −4 |
| upper 1st bic. | 0.044 | 0 | 0.042 | −2 |
| upper 2nd bic. | 0.050 | 0 | 0.052 | 0 |
| upper 1st molar | 0.041 | 15 | 0.041 | 15 |
| upper 2nd molar | 0.041 | 15 | 0.041 | 15 |
| lower central | 0.045 | 0 | 0.050 | 0 |
| lower lateral | 0.045 | 0 | 0.050 | 1 |
| lower cuspid | 0.045 | −4.5 | 0.038 | −6 |
| lower 1st bic. | 0.046 | 0 | 0.045 | −1 |
| lower 2nd bic. | 0.049 | 0 | 0.050 | 0 |
| lower 1st molar | 0.041 | 0 | 0.041 | 0 |
| lower 2nd molar | 0.041 | 4 | 0.041 | 0 |

As a further refinement that is particularly feasible when custom orthodontic appliances are being designed and manufactured, in step (190), the bottom 34 of the slot 33 of each bracket 30 is not only inclined at the rotation angle RA but is also curved to conform to the curvature of the archwire along the entire archwire slot 33 of the bracket 30. Such slot bottom curvature will be tangent to the archwire curve 28 and thus inclined at the rotation angle RA at its intersection with the line CPP, and will other wise conform to the curvature, represented by radii $R_3$ and $R_4$ of two circle segments $C_3$ and $C_4$ of the archwire curve 28, to the extent that these segments lie in the slot 33. Such a slot bottom 34a, having such a rotation angle and an archwire curve conforming shape, is illustrated, with an exaggerated curve, in FIG. 6.

Figure 7:
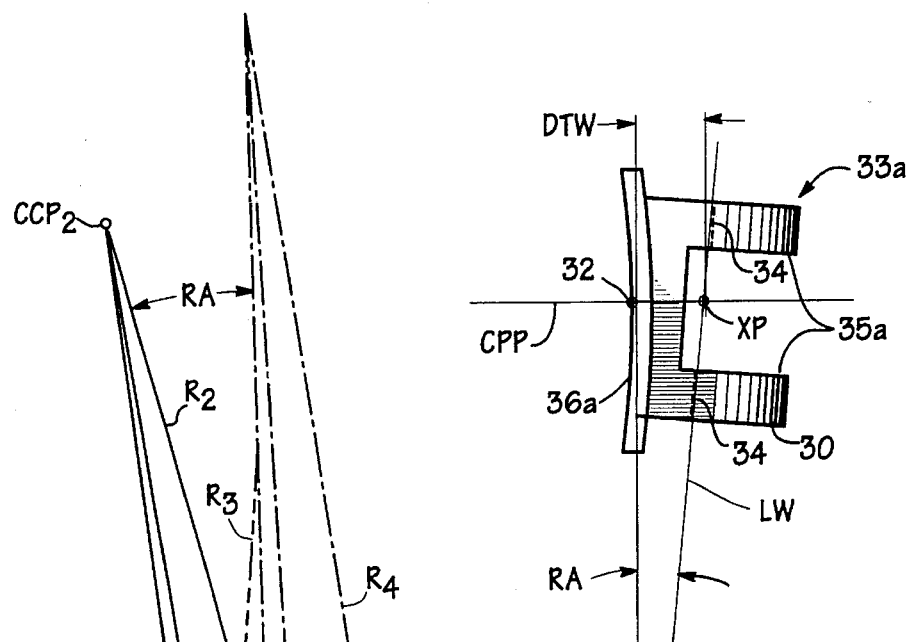
FIG. 7 is a top view of still another embodiment of the bracket of FIG. 5.

The brackets of FIG. 5 are formed with the slots sloped relative to the bracket supports or wings 35, which are shown extending perpendicularly relative to the bracket base surface 36. In the embodiment of FIG. 7, the wings or supports 35a are inclined relative to the base 36 at the same angle as the slot 33a. From a fabrication point of view, the rotation is achieved by forming the base 36a, rather than the slot 33 of FIG. 5, at an angle relative to the supports 35a.

In order to treat patients with the low profile appliance, as described above, brackets are selected for mounting on the teeth of the patient to support an archwire at a spacing of not more than 0.06 inches from the mounting surface of the tooth, and preferably at not more than approximately 0.05 inches from the mounting surface of any of the teeth, measured from the center of the bracket base labially to the centerline of the archwire, for archwires generally in the range of standard diameters of 0.018 and 0.022 inches. The spacing for the upper lateral bracket is generally larger than that of the other brackets. Preferably, the tooth to archwire distance is in the range of 0.03 to 0.04 for several of the teeth, and therefore averages not much more than approximately 0.040 inches.

For custom appliances, the slot rotation angle is custom cut into each bracket, and is usually calculated to be one degree or more, more often in the negative or mesial direction. With standardized appliances, due to the compromising nature of standardized brackets, need not be provided in each of the brackets, but only in one bracket in the vicinity of the lateral, cuspid, or first bicuspid, as it has been found that a negative slot rotation of approximately 4 to 8 degrees on the upper lateral and on the lower cuspid are sufficient to cause more than adequate convergence of the archwire adjacent the incisors to produce an improved low profile appliance. Particularly in Asian patients, a negative rotation distributed over rotation that is distributed among the lateral, cuspid and first bicuspid is preferable.

To provide treatment with the low profile appliance, the brackets are preferably selected such that the archwire converges toward the dental archform adjacent the central teeth. As such, the slot bottom rotation angles may be approximately 0° adjacent the central teeth, and also adjacent one or more of the second bicuspids or molars, but will be generally negative (that is, inclined mesially on the labial side of the tooth) somewhere in the vicinity of the laterals, cuspids and first bicuspids, being inclined a total (algebraically) of 4° to 8° adjacent these three teeth on each side of a dental arch. Generally, and for the lower arch particularly, the lowest profile is obtained where the rotation angle is most negative proximate the cuspid, for example, −4.5° or 6°, with additional rotation distributed over one or both of the teeth adjacent to the cuspid.

From the above detailed description of the preferred embodiments of the invention, those skilled in the art will appreciate that modifications and additions to that described above may be employed without departing from the principles of the present invention.

Therefore, the following is claimed:

1. A method of making an orthodontic appliance for straightening the teeth of a patient, the method comprising the steps of:

determining shapes of the teeth to be straightened;

determining finish positions, in a dental archform, to which the teeth of the patient are to be moved by the appliance;

determining bracket mounting points, one on each of the teeth of the patient;

deriving, from the determined tooth shapes, finish positions and mounting points, archwire geometry having a smooth arcuate shape designed to pass the center of the archwire within a distance that is not more than approximately 0.05 inches from each of the bracket mounting points of substantially all of the teeth on a dental arch of the patient when the teeth of the patient are in the determined finish positions, the arcuate shape converging with the archform adjacent an anterior one of the teeth;

fabricating a plurality of brackets, one for connection to each tooth at the bracket mounting point thereon, each bracket having a bracket base configured to connect to the bracket mounting point on the respective tooth and an archwire slot formed in the bracket extending to a slot bottom positioned to support the archwire in the slot within the distance of the bracket mounting surface of the bracket; and the bracket fabricating step including the step of fabricating at least one bracket for a cuspid or tooth adjacent a cuspid that is sloped at an angle of rotation that is negative relative to the bracket base, to support therein an archwire so shaped to converge with the archform mesial thereto.

2. The method of claim 1 further comprising the steps of:

securing each of the fabricated brackets to a respective tooth on the lower arch of the patient at the bracket mounting point thereon; and supporting the archwire in the slots of the fabricated brackets on the teeth of the patient.

3. The method of claim 1 wherein:

the bracket fabricating step includes the step of forming the slot bottom of at least one of the brackets to a negative rotation angle, to slope the slot bottom in a mesial direction toward the bracket base, of at least 4°.

4. The method of claim 1 wherein:

the bracket fabricating step includes the steps of fabricating the brackets each having a base and then forming the slot in the bracket at the rotation angle relative to the base.

5. The method of claim 1 wherein:

the bracket fabricating step includes the steps of fabricating the brackets each having a slot therein and then forming the base of the bracket at the rotation angle relative to the slot.

6. The method of claim 1 wherein:

the bracket fabricating step includes the step of fabricating the brackets such that the spacing from the base thereof to the archwire of no bracket other than for an upper lateral is more than 0.05 inches.

7. An orthodontic appliance for straightening the teeth of a patient to relative finish positions, comprising:

an archwire having a smooth arcuate shape;

a plurality of brackets, one for connection to each of a plurality of the teeth of the patient at a bracket mounting point thereon, each bracket having a mounting surface configured to fit the respective tooth at the bracket mounting point and an archwire slot formed therein extending to a slot bottom positioned to support the archwire in the slot within a distance that is not more than approximately 0.06 inches of the mounting surface of a bracket for an upper lateral and not more than approximately 0.05 inches of the bracket mounting surfaces of brackets for teeth other than upper laterals; and the slot bottom of at least one bracket for a cuspid or tooth adjacent a cuspid being sloped at an angle of rotation that is negative relative to the bracket base, to support an archwire so shaped to converge with the archform mesial thereto.

8. The appliance of claim 7 wherein:

the slot bottom of each of the brackets for the teeth within one tooth of a cuspid having rotation angles the sum of which is at least negative 4°.

9. The appliance of claim 7 wherein:

the slot bottoms of the brackets for the lower cuspids each having a rotation angle that is at least negative 4°.

10. The appliance of claim 7 wherein:

the slot bottoms of the brackets for the upper laterals each having a rotation angle of at least negative 3°.

11. The appliance of claim 7 wherein:

slot bottoms of the brackets for the each tooth within one tooth of an upper cuspid having rotation angles, the algebraic sum of which is at least negative 4°.

12. The appliance of claim 7 wherein:

each bracket for a lower tooth has the archwire slot therein formed to a slot bottom positioned to support the archwire in the slot within a distance that is not more than approximately 0.05 inches of the mounting surface of the bracket.

13. The appliance of claim 7 wherein:

each bracket for each tooth other than an upper lateral has the archwire slot therein formed to a slot bottom positioned to support the archwire in the slot within distance that is not more than approximately 0.05 inches of the mounting surface of the bracket.

14. The appliance of claim 7 wherein:

the brackets are dimensioned such that the average of the distances from the slot bottoms of the brackets to the respective mounting surfaces thereof average not more than 0.045 inches.

15. A set of orthodontic brackets for use in an orthodontic appliance for straightening the teeth of a patient to relative finish positions, comprising:

a plurality of brackets, one for connection to each of a plurality of the teeth of the patient at a bracket mounting point thereon, each bracket having:

a mounting surface configured to fit the respective tooth at the bracket mounting point, and an archwire slot formed therein extending to a slot bottom, which, for the lower teeth, is positioned to support the archwire in the slot within distance that is not more than approximately 0.05 inches of the bracket mounting surface; and the slot bottoms of at least one bracket for a cuspid or tooth adjacent thereto having a negative rotation angle.

16. The bracket set of claim 15 wherein:

the plurality of brackets includes brackets having mounting surfaces configured for connection at the bracket mounting points on the cuspids and teeth adjacent thereto, the algebraic sum of the rotation angles of the slot bottoms of which is between −4° and −10° C.

* * * * *

UNITED STATES PATENT AND TRADEMARK OFFICE
CERTIFICATE OF CORRECTION

PATENT NO. : 5,474,448
DATED : December 12, 1995
INVENTOR(S) : Craig A. Andreiko, et al.

It is certified that error appears in the above-indentified patent and that said Letters Patent is hereby corrected as shown below:

Column 5, line 24, delete "14M" and insert --$14_M$--.

Column 5, line 25, delete "14D" and insert --$14_D$--.

Column 7, line 33, delete "CCP" and insert --$CCP_1$--.

Column 9, line 65, insert --XP-- after point.

In the claims:

Column 12, line 50, delete "negative 4°" and insert --4° negative--.

Column 12, line 53, delete "negative 4° and insert --4° negative--.

Column 12, line 56, delete "negative 3° and insert --3° negative--.

Column 12, line 61, delete "negative 4°" and insert --4° negative--.

UNITED STATES PATENT AND TRADEMARK OFFICE
CERTIFICATE OF CORRECTION

PATENT NO. : 5,474,448
DATED : December 12, 1995
INVENTOR(S) : Craig A. Andreiko, et al.

It is certified that error appears in the above-indentified patent and that said Letters Patent is hereby corrected as shown below:

Column 14, line 16, delete "C" after -10°.

Signed and Sealed this

Seventeenth Day of September, 1996

Attest:

BRUCE LEHMAN

Attesting Officer

Commissioner of Patents and Trademarks